(12) United States Patent
Snodgrass et al.

(10) Patent No.: US 10,632,091 B2
(45) Date of Patent: Apr. 28, 2020

(54) DOSAGE FORMS AND THERAPEUTIC USES OF L-4-CHLOROKYNURENINE

(71) Applicant: VISTAGEN THERAPEUTICS, INC., South San Francisco, CA (US)

(72) Inventors: H. Ralph Snodgrass, South San Francisco, CA (US); Allen E. Cato, Durham, NC (US); Jack S. Hicklin, San Diego, CA (US)

(73) Assignee: VISTAGEN THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 15/978,855

(22) Filed: May 14, 2018

(65) Prior Publication Data

US 2019/0125707 A1 May 2, 2019

Related U.S. Application Data

(62) Division of application No. 14/762,015, filed as application No. PCT/US2014/012598 on Jan. 22, 2014, now Pat. No. 9,993,450.

(60) Provisional application No. 61/849,191, filed on Jan. 22, 2013.

(51) Int. Cl.
 *A61K 31/198* (2006.01)
 *A61K 9/00* (2006.01)

(52) U.S. Cl.
 CPC .......... *A61K 31/198* (2013.01); *A61K 9/0053* (2013.01)

(58) Field of Classification Search
 USPC ........................................................ 514/564
 See application file for complete search history.

(56) References Cited

U.S. PATENT DOCUMENTS

| | | | |
|---|---|---|---|
| 5,470,870 | A | 11/1995 | Palfreyman et al. |
| 5,547,991 | A | 8/1996 | Palfreyman |
| 5,763,393 | A | 6/1998 | Moskal et al. |
| 7,250,394 | B2 | 7/2007 | Nedergaard |
| 8,680,042 | B2 | 3/2014 | Bogdanova et al. |
| 8,951,968 | B2 | 2/2015 | Moskal |
| 9,745,342 | B2 | 8/2017 | Khan |
| 2006/0063802 | A1 | 3/2006 | Guitton et al. |
| 2007/0244177 | A1 | 10/2007 | Thormann et al. |
| 2008/0286231 | A1 | 11/2008 | Buchholz et al. |
| 2009/0076019 | A1 | 3/2009 | Tyers et al. |
| 2010/0234397 | A1 | 9/2010 | Thormann et al. |
| 2011/0306674 | A1 | 12/2011 | Schiene et al. |
| 2012/0282592 | A1 | 11/2012 | Kawamura et al. |
| 2014/0018348 | A1 | 1/2014 | Javitt |
| 2018/0140568 | A1 | 5/2018 | Snodgrass et al. |

FOREIGN PATENT DOCUMENTS

| | | |
|---|---|---|
| CA | 2615271 C | 2/2011 |
| EP | 1903028 A1 | 3/2008 |
| JP | 6-501454 | 2/1994 |
| WO | 91/19493 A1 | 12/1991 |
| WO | 2004/022069 A1 | 3/2004 |
| WO | 2014/116739 A1 | 7/2014 |
| WO | 2014/152835 A1 | 9/2014 |
| WO | 2016/191351 A1 | 1/2016 |

OTHER PUBLICATIONS

Tinazzi (Pain and motor complications in Parkinson's disease, J Neurol Neurosurg Psychiatry 2006;77:822-825).*
MarketWatch:CNS: Epilepsy Update, VistaGen receives $3.7 million for epilepsy research; Datamonitor, Jul. 2005.
MarketWatch:CNS: VistaGen secures support for Huntington's drug development; Datamonitor, Sep. 2005.
MarketWatch:Pharmaceuticals: CNS News Round-Up; Datamonitor, Jan. 2007.
MarketWatch:CNS: VistaGen says data supports expanded drug application; Datamonitor, Jan. 2007.
MarketWatch:CNS: VistaGen to extend neurologic drug for Parkinson's treatment; Datamonitor, Dec. 2007.
Malkesman et al., "Acute D-serine treatment produces antidepressant-like effects in rodents", Int J. Neuropsychopharmacol. Sep. 2012 ; 15(8): 1135-1148.
Seromycin Prescribing Information, https://dailymed.nlm.nih.gov/dailymed/fda/fdaDrugXsl_cfm?setid=e1e08327-4b90-463e-bb2a-22438cabcef2&type=display, pp. 1-7, revised Oct. 2011, accessed.
Perahia et al., "Duloxetine in the prevention of relapse of major depressive disorder", British Journal of Phychiatry (2006) 188, pp. 344-353.
Christoph et al., "Antiallodynic effects of NMDA glycineB antagonists in neuropathic pain: Possible peripheral mechanisms", Brain Research, 1048 (2005), pp. 218-227.
Rundfeldt "Anticonvulsant activity of antagonists and partial agonist for the NMDA receptor-associated glycine site in the kindling model of epilepsy", Brain Research, vol. 653, Issue 1-2, 1994.
Catarzi "Competitive GLY/NMDA Receptor Antagonist", vol. 6, Issue 8 (abstract only), accessed Jan. 23, 2018.
Extended European Search Report for EP Application No. 17170079. 2, dated Sep. 7, 2017.
Dunkel et al., "Clinical utility of neuroprotective agents in neurodegenerative diseases: current status of drug development for Alzheimer's, Parkinson's and Huntington's diseases, and amyotrophic lateral sclerosis", Expert Opin. Investig. Drugs, 2012, 21(9), pp. 1267-1308.
Poewe et al., "Levodopa in the treatment of Parkinson's disease: an old drug still going strong", Clinical Interventions in Aging, 2010, Doverpress, pp. 229-238.
Lapidus et al., "Novel glutamatergic drugs for the treatment of mood disorders," Neuropsychiatric Disease and Treatment, 2013, 9, pp. 1101-1112.
Limapichat et al., "Key Binding Interations for Memantine in the NMDA Receptor," ACS Chem. Neurosci. 2013, 4, pp. 255-260.

(Continued)

*Primary Examiner* — Kathrien A Cruz
(74) *Attorney, Agent, or Firm* — J. A. Lindeman & Co. PLLC

(57) ABSTRACT

Compositions of L-4-chlorokynurenine are provided, as are methods for the treatment of neurologica dyslinction.

6 Claims, 2 Drawing Sheets

(56) References Cited

OTHER PUBLICATIONS

Papp et al., "Antidepressant activity of non-competitive and competitive NMDA receptor antagonists in a chronic mild stress model of depression," Eur. J. Pharm., 263, 1994, pp. 1-7.
Poleszak et al., "A Complex interaction between glycine/NDMA receptors and serotonergic/noradrenergic antidepressants in the forced swim test in mice", J. Neural. Transm., 2011, 118: pp. 1535-1546.
Przefalinski et al., "Antidepressant-like Effects of a Partial Agonist at Strychnine-insensitive Glycine Receptors and a Competitive NMDA Receptor Antagonist," Neuropharmacology, 1997, vol. 36, No. 1, pp. 31-37.
Reisberg et al., "T1. Clinical Staging with the Global Deterioration Scale (GDS) Shows a Remarkably Uniform Pattern of Temporal Change Over 2 Years in Healthy Older Persons with Subjective Cognitive Impairment (SCI) in Accord with Prior Estimates and Observations Indicating a Stage of 15 Years Duration," Neuropsychopharmacology, 2015, 40, pp. S272-S442, Abstract.
Skolnick at eal., "Glutamate-based antidepressants: 20 years on," Trends in Pharmacological Sci. vol. 30, No. 11, pp. 563-569.
Trullas et al., "Functional antagonists at the NMDA receptor complex exhibit antidepressant actions," Eur. J. Pharm. 1990, 185, pp. 1-10.
Extended European Search Report in corresponding EP Application No. 14743570, dated Jul. 1, 2016.
McDonald et al., "HA-966 (1-hydroxy-3-aminopyrrolidone-2) selectively reduces N-methyl-D-aspartate (NMDA)-mediated brain damage," Neurosc. Letters 104: 167-170 (1989).
Menon, "Demonstration of the antimyoclonic effect of 1-hydroxy-3-amino-pyrrolidone-2 (HA-966) using a New animal model," Life Sci. 28:2865-2868 (1981).
Vlurrough et al., "Antidepressant Efficacy of Ketamine in Treatment-Resistant Major Depression: A Two-Site Randomized Controlled Trial," Am. J. Psychiatry 170: 1134-1142 (2013).
Schwarcz et al. "Kynurenines in the Mammalian Brain: When Physiology Meets Pathology," Nat Rev Neurosci 13(7): 465-477 (2012).
Zarate et al., "A Randomized Trial of an N-methyl-D-aspartate Antagonist in Treatment-Resistant Major Depression," Arch Gen Psychiatry 63: 856-864 (2006).
Gerhard et al., "Emerging treatment mechanisms for depression: focus on glutamate and synaptic plasticity," Drug Discov Today 21: 454-464 (2016).
Bay-Richter et al., "A role for inflammatory metabolites as modulators of the glutamate N-methyl-d-aspartate receptor in depression and suicidality," Brain Behav Immun 43: 110-117 (2015).
Preskorn et al., "Randomized Proof of Concept Trial of GLYX-13, an N-Methyl-D-Aspartate Receptor Glycine Site Partial Agonist, in Major Depressive Disorder Nonresponsive to a Previous Antidepressant Agent," J Psychiatr Pract 21: 140-149 (2015).
Moskal et al., "GLYX-13: A monoclonal antibody-derived peptide that acts as an N-methyl-d-aspartate receptor modulator," Neuropharmacology 49: 1077-1087 (2005).
Banerjee et al., "Rapastinel (Glyx-13), a Rapid Acting Antidepressant, Does not Increase Extracellular Levels of Dopamine and Glutamate in Rat Medial Prefrontal Cortex," Neuropsychopharmacology (2016) 41, Abstract M45, p. S151.
Donello et al., "Rapastinel (Glyx-13), a Rapid Acting Antidepressant, Exhibits Co-Agonist Properties at NMDA Receptors Independent of the Glycine Co-Agonist Binding Site," Neuropsychopharmacology (2016) 41, Abstract M58, p. S153-S154.
Nina Notman "The K factor—How the party drug ketamine may hold the key to treating patients with severe depression, " Chemistry World, Mar. 4, 2017, pp. 1-13.
Jian-Shu Lou et al., The mediation of immune activation on serotonin and glutamate systems in pathological process of depression. Chinese Pharmacological Bulletin. 2009(12): 1555-8.
Ning-Na Zhou et al., A new target for treatment of depression. Journal of Psychiatry. 2009, 22(2): 153-157.

Ates-Alagoz et al., "NMDA Receptor Antagonists for Treatment of Depression", Pharmaceuticals 2013, 6, pp. 480-499.
Barba et al., "Swelling of cellulose derivative (HPMC) matrix systems for drug delivery", Carbohydrate Polymers 78 (2009) pp. 469-474.
Baron et aL, "Activity of 5,7-Dichiorokynurenic Acid, a Potent Antagonist at the N-Methyl-D-aspartate Receptor-Associated Glycine Binding Site", Molecular Pharmacology, (1990) 38, pp. 554-561.
Carpenedo et al., "Inhibitors of Kynurenine Hydroxylase and Kynureninase Increase Cerebral Formation of Kynurenate and Have Sedative and Anticonvulsant Activities", Neuroscience, vol. 61, No. 2, pp. 237-244, 1994.
Chen et al., "Kynurenine Pathway Metabolites in Humans: Disease and Healthy States", International Journal of Tryptophan Research 2009:2, pp. 1-19.
Christoph et al., "The antiallodynic effect of NMDA antagonists in neuropathic pain outlasts the duration of the in vivo NMDA antagonism", Neuropharmacology 51, 2006, pp. 12-17.
Foster et al., "Kynurenic Acid Analogues with Improved Affinity and Selectivity for the Glycine Site on the N-Methyl-D-aspartate Receptor from Rat Brain", Molecular Pharmacology, 41, pp. 914-922, 1992.
Donello et al., Abstracts 2016.
Hay et al., "Clinical development success rates for investigational drugs", Nature Biotechnology, vol. 31, No. 1, Jan. 2014.
Kehne et al., "NMDA receptor complex antagonists have potential anxiolytic effects as measured with separation-induced ultrasonic vocalizations", European Journal of Pharmacology, 193 (1991) pp. 283-292.
Kotlinska et al., "A characterization of antiolytic-like actions induced by the novel NFDA/glycine site antagonist, L-701,324", Psychopharmacology (1998) 135, pp. 175-181.
Kretschmer et al., "Glycine site antagonists abolish dopamine D 2 but not D 1 receptor mediated catalepsy in rats", Journal of Neural Transmission, [GenSect] (1994) 95, pp. 123-136.
Laugeray et al., "Evidence for a key role of the peripheral kynurenine pathway in the modulation of anxiety- and depression-like behaviours in mice: Focus on individual differences", Pharmacology, Biochemistry and Behavior 98 (2011) pp. 161-168.
Leeson et al., "The Glycine Site on the NMDA Receptor: Structure-Activity Relationships and Therapeutic Potential", Journal of Medicinal Chemistry, vol. 37, No. 24, Nov. 25, 1994, pp. 4053-4067.
Li et al., "mTOR-Dependent Synapse Formation Underlies the Rapid Antidepressant Effects of NMDA Antagonists", Science, New Series, vol. 329, No. 5994 (Aug. 20, 2010), pp. 959-964.
Linderholm et al., "Role of the NMDA-receptor in Prepulse Inhibition in the Rat", International Journal of Tryptophan Research, 2010:3, pp. 1-12.
Maj et al., "Some Central Effects of Kynurenic Acid, 7-Chlorokynurenic Acid and 5,7-Dichloro-Kynurenic Acid, Glycine Site Antagonists", Pol J Pharmacol 46 (3), pp. 115-124. May-Jun. 1994.
Millan, "N-Methyl-D-aspartate receptors as a target for improved antipsychotic agents: novel insights and clinical perspectives", Psychopharmacology (2005) 179, pp. 30-53.
Paul et al., "Glutamate and Depression Clinical and Preclinical Studies", Ann. N.Y. Acad. Sci. 1003, pp. 250-272 (2003).
Preskorn et al., "An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder", J Clin Psychopharmacol 2008, 28, pp. 631-637.
Schade et al., "D-Cycloserine in Neuropsychiatric Diseases: A Systematic Review", International Journal of Neuropsychopharmacology, (2016) 19(4) pp. 1-7.
Skolnick, "Modulation of glutamate receptors: Strategies for the development of novel antidepressants", Sep. 2002, vol. 23, Issue 1-3, pp. 153-159.
Stone et al., "Kynurenine pathway inhibition as a therapeutic strategy for neuroprotection", FEBS Journal 279 (2012) pp. 1386-1397.
Wiley et al., "Effects of site-selective NMDA receptor antagonists in an elevated plus-maze model of anxiety in mice", European Journal of Pharmacology 294 (1995) pp. 101-107.

(56) References Cited

OTHER PUBLICATIONS

Young, "Neuroprotective effects of antidepressant and mood stabilizing drugs", J. Psychiatry Neurosci 2002:27(1) pp. 8-9.
Parsons et al., "Novel Systemically Active Antagonists of the Glycine Site of the N-Methyl-D-aspartate Receptor: Electrophysiological, Biochemical and Behavioral Characterization" The Journal of Pharmacology and Experimental Therapeutics; vol. 283, No. 3, 1997.
Shimizu et al., "Glycine-Binding Site Stimulants of NMDA Receptors Alleviate Extrapyramidal Motor Disorders by Activating the Nigrostriatal Dopaminergic Pathway", Int. J. Mol. Sci. 2017, 18, 1416.
Zanos P. et al., "4-Cl-Kynurenine, a Pro-Drug of a Selective Glycineb NMDA Receptor Antagonist, Induces Rapid and Sustained Antidepressant Effects without Ketamine-related Side Effects", Neuropsychopharmacology, 2-14, vol. 39, pp. S618-S619.
Guitton et al., "m-Chlorophenylpiperazine exacerbates perception of salicylate-induced tinnitus in rats", European Journal of Neuroscience, vol. 22, No. 10, 2005, pp. 2675-2678.
Zhu et al., "Glycine site N-methyl-D-asparate receptor antagonist 7-CTKA produces rapid antidepressant-like efffects in male rats", Journal of Psychiatry and Neuroscience, vol. 38, No. 5, 2013, pp. 306-316.
Safety, Tolerability and Pharmacokinetics of Multiple Doses of AV-101 in Healthy Volunteers, CinicalTrials.gov, ClinicalTrials.gov Identifier: NCT01483846, Available from the Internet, <URL: https://clinicaltrials.gov/ct2/show/NCT01483846>, Dec. 1, 2011.
PUBCHEM, 4CHLOROKYNURENINE, 2006, p. 3, formula.
Robinson et al., "Antidepressant therapy in tinnitus", Hearing Research, 2007, vol. 226, pp. 221-231.
Saxena et al., "Differential Cerebral Metabolic Changes with Paroxetine Treatment of Obsessive-Compulsive Disorder vs Major Depression", Archives of General Psychiatry, 2002, vol. 59, pp. 250-261.
International Preliminary Report on Patentability in International Application No. PCT/US2014/012598, dated Aug. 6, 2015.
International Search Report and Written Opinion in International Application No. PCT/US2014/012598, dated Feb. 24, 2014.
Linderholm et al., "Activation of rat ventral tegmental area dopamine neurons by endogenous kynurenic acid: A pharmacological analysis," Neuropharmacology (2007), vol. 53, p. 918-924.
Wu et al., "L-4-Chlorokynurenine Attenuates Kainate-Induced Seizures and Lesions in the Rat," Experimental Neurology (2002), vol. 177, p. 222-232.
Wu et al., "Systemic administration of 4-chlorokynurenine prevents quinolinate neurotoxicity in the rat hippocampus," European J. of Pharmacology (2000), vol. 390, p. 267-274.
Zhang et al., "In Situ-Produced 7-Chlorokynurenate Has Different Effects on Evoked Responses in Rats with Limbic Epilepsy in Comparison to Naive Controls," Epilepsia (2005), vol. 46(11), p. 1708-1715.
Calabrese et al., "Stress-Induced Changes of Hippocampal NMDA Receptors: Modulation by Duloxetine Treatment," PLOS One, May 2012, vol. 7, Issue 5, e37916.
Hokari et al., "Faciliated brain uptake of 4-chlorokynurenine and conversion to 7-chlorokynurenic acid," NeuroReport, vol. 8, No. 1, Dec. 20, 1996, pp. 15-18.
Kemp et al., "7-Chlorokynurenic acid is a selective antagonist at the glycine modulatory site of the N-methyl-D-aspartate receptor complex," Proc. Natl., Acad. Sci., vol. 85, Sep. 1988, pp. 6547-6550.
Lee et al., "Excitotoxic injury stimulates pro-drug-induced 7-chlorokynurenate formation in the rat striatum in vivo," Nuroscience Letters 304, (2001), pp. 185-188.
Vistagen "VistaGen Therapeutics Inc. (VSTA) on Path to Higher Exchange," WooEB Community Message Boards, post by MissionIR, Sep. 6, 2011.
VistaGen "VistaGen Therapeutics Reports Identification of Cell Surface Marker That Permits High-Yield Purification of Human Pluripotent Stem Cell-Derived Cardiomyocytes," InvestoStemCell, Oct. 25, 2011.
VistaGen "VistaGen Therapeutics Engages Mission IR as Its Investor Relations Advisor," Press Release, Feb. 22, 2012.
VistaGen "VistaGen Therapeutics (VSTA) Develops New Approach to Major Neurological Market," TransWorldNews, Mar. 2, 2012.
VistaGen "VistaGen (VSTA) Goes Beyond Drug Testing," TheLion.com, Aug. 2, 2012.
VistaGen "VistaGen Therapeutics, Inc. (VSTA)," QualityStocks, Oct. 2012.
H. Ralph Snodgrass "AV-101 (L-4-cholokynurenine) A prodrug for treating pain," Presentation at NIH Pain Consortium Symposium, May 2012.
Wu et al., "Kynurenate and 7-Chlorokynurenate Formation in Chronically Epileptic Rates," Epilepsia, vol. 46, No. 7, (2005), pp. 1-7.
Guidetti et al., "In Situ Produced 7-Chlorokynurenate Provides Protection against Quinolinate- and Malonate-Indcued Neurotoxicity in the Rat Striatum," Experimental Neurology 163, 123-130 (2000).
Kohl et al., "The NMDA Receptor Complex: A Promising Target for Novel Antiepileptic Stragegies," Current Medicinal Chemistry, 2001, 8, pp. 1275-1289.
Nabavi et al., "Metabotropic NMDA receptor function is required for NMDA receptor-dependent long-term depression," PNAS, Mar. 5, 2013, vol. 110, No. 10, pp. 4027-4032.
Tan et al., "The kynurenine pathway in neurodegenerative diseases: Mechanistic and therapeutic considerations," J. Neurological Sci., 323, (2012), pp. 1-8.
Vamos et al., "The role of kynurenines in disorders of the central nervous system: Possibilities for neuroprotection," J. Neuroligical Sci., 283, (2009), pp. 21-27.
Wu et al., "Enzyme-catalyzed production of the neuroprotective NMDA receptor antagonist 7-chlorokynurenic acid in the rat brain in vivo," European J. of Pharm., 319, (1997), pp. 13-20.
Dubrovina et al., "N-Methyl-D-Aspartate Receptors and Amnesia in Mice with Depression-Like State," Bulletin of Experimental Biology and Medicine, vol. 144, No. 5, (2007), pp. 647-649.
Jansen et al., "Antagonists and agonists at the glycine site of the NMDA receptor for therapeutic interventions," European J. of Medicinal Chemistry, 38, (2003), pp. 661-670.
Parsons, "NMDA receptors as targets for drug action in neuropathic pain," European J. of Pharmacology, 429, (2001), pp. 71-78.
Pittenger et al., "The NMDA Receptor as a Therapeutic Target in Major Depressive Disorder," CNS & Neurological Disorders—Drug Targets, 2007, 6, pp. 101-115.
Schwarcz et al., "Manipulation of Brain Kynurenines: Glial Targets, Neuronal Effects, and Clinical Opportunities," J. of Pharmacology and Experimental Therapeutics, Vo. 303, No. 1, (2002), pp. 1-10.
Vecsei et al., "Kynurenines in the CNS: recent advances and new question," Nature, 64, Jan. 2013, vol. 12, pp. 64-82.
Nemeth et al., "Kynurenines, Parkinson's disease and other neurodegenerative disorders: preclinical and clinical studies," J. Neural Transm. Suppl. 2006 (70) pp. 285-304.
Stone, "The development and therapeutic potential of kynurenic acid and kynurenine derivatives for CNS neuroprotection," Trends Pharmacol Sci 2000 (21) pp. 149-154.
Bristow et all., "Anticonvulsant and Behaviorial Profile of L-701,324, a Potent, Orally Active Antagonist at the Glycine Modulatory Site on the N-Methyl-D-aspartate Receptor Complex," J. of Pharm. and Experimental Therapeutics, 1996, vol. 279, No. 2, pp. 492-501.
Burgdorf et al., "GLYX-13, a NMDA Receptor Glycine-Site Functional Partial Agonist, Induces Antidepressant-Like Effects Without Ketamine-Like Side Effects," Neuropsychopharmacology, 2013, 38, pp. 729-742.
Danysz et al., "Glycine and N-Methyl-D-Aspartate Receptors: Physiological Significance and Possible Therapeutic Applications," Pharmacological Reviews, 1998, vol. 50, No. 4, pp. 597-664.
Garcia et al., "Acute Administration of ketamine induces antidepressant-like effects in the forced swimming test and increases BDNF levels in the rat hippocampus," Progress in Neuro-Psychopharmacology & Biological Psychiatry, 2008, 32, pp. 140-144.
Stuart A. Lipton "Failures and Successes of NMDA Receptor Antagonists: Molecular Basis for the Use of Open-Channel Blockers like Memantine in the Treatment of Acute and Chronic Neuro-

(56) References Cited

OTHER PUBLICATIONS logic Insults," Am. Soc. for the Experimental NeuroTherapeutics, Inc., Jan. 2004, vol. 1, pp. 101-110.

Maj et al., "Effects of MK-801 and antidepressant drugs in the forced swimming test in rats," European Neuropsychopharmacology, 1992, 2, pp. 37-41.

Moryl et al., "Potential Antidepressive Properties of Amantadine, Memantine and Bifemelane," Pharmacology & Toxicology, 1993, 72, pp. 394-397.

Petit-Demouliere et al., "Forced swimming test in mice: a review of antidepressant activity," Psychopharmacology, 2005, 177, pp. 245-255.

Przegalinski et al., "Anxiolytic- and Antidepressant-Like Effects of an Antagonist at Glycine Receptors," Pol. J. Pharmacol., 1998, 50, pp. 349-354.

Santangelo et al., "Novel NMDA Receptor Modulators: An Update," Expert Opin. Ther. Pat. 22(11): 1337-1352 (2012).

Sleigh et al., "Ketamine—More mechanisms of action than just NMDA blockade," Trends in Anaesthesia and Critical Care 4, (2014), pp. 76-81.

Zanos et al., "The Prodrug 4-Chlorokynurenine Causes Ketamine-Like Antidepressant Effects, but Not Side Effects, by NMDA/Glycineb-Site Inhibition," J. Pharamcol. Exp. Ther., Oct. 2015, 355, pp. 76-85.

Zarate et al., "A Double-Blind, Placebo-Controlled Study of Memantine in the Treatment of Major Depression," Am. J. Psychiatry, 2006, 163, pp. 153-155.

Chu et al., "Species differences in drug transporters and implications for translating preclinical findings to humans," Expert Opin. Drug Metab. Toxicol., 2013, vol. 9, No. 3; pp. 237-252.

Grossberg et al., "The Safety, Tolerability, and Efficacy of Once-Daily Memantine (28 mg): A Multinational, Randomized, Double-Blind, Placebo-Controlled Trial in Patients with Moderate-to-Severe Alzheimer's Disease Taking Cholinesterase Inhibitors," DNS Drugs, 2013, 27, pp. 469.478.

Heresco-Levy et al., "Controlled trial of D-cycloserine adjuvant therapy for treatment-resistant major depressive disorder," J. Affective Disorders, 93, 2006, pp. 239-243.

Heresco-Levy et al., "A randomized add-on trial of high-dose D-cycloserine for treatment-resistant depression," International J. Neuropsychopharmacology, 2013, 16, pp. 501-506.

Konieczny et al., "L-701,324, a selective antagonist at the glycine site of the NMDA receptor, counteracts haloperidol-induced muscle rigidity in rats," Psychopharmacology 1999, 143, pp. 235-243.

Tambasco et al., "Clinical Aspects and Management of Levodopa-Induced Dyskinesia," Review Article, Hindawi Publishing Corporation, Parkinson's Disease, 2012, ID 745947, pp. 1-12.

Tinazzi et al., "Pain and motor complications in Parkinson's disease", J. Neurol. Neurosurg. Psychiatry, 2006, 77:822-825.

Morissette et al., "Prevention of Dyskinesia by an NMDA Receptor Antagonist in MPTP Monkeys: Effect on Adenosine A2A Receptors", Synapse, 2006, 60: pp. 239-250.

Nutt et al., "Effects of a NR2B Selective NMDA Glutamate Antagonist, CP-101, 606, on Dyskinesia and Parkinsonism", Mov. Disord. 2008, 15; 23(13): pp. 1860-1866.

Kekesi et al., "The antinociceptive effect of intrathecal kynurenic acid and its interaction with endomorphin- 1 in rats", European Journal of Pharmacology, 445, 2002, pp. 93-96.

Ren et al., "The intrathecal administration of excitatory amino acid receptor antagonists selectively attenuated carrageenan-induced behavorial hyperalgesia in rats", European Journal of Pharmacology, 219, 1992, pp. 235-243.

* cited by examiner

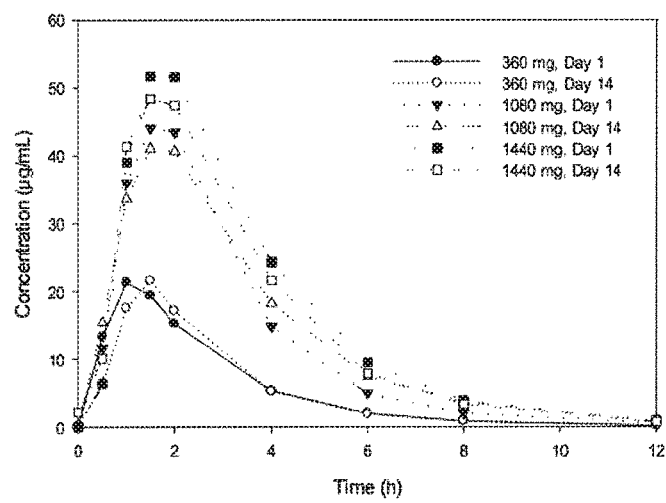
Figure 1. Mean (n = 12 or 13) plasma concentrations of L-4-chlorokynurenine on Days 1 and 14 after oral administration of once-daily doses of AV-101.

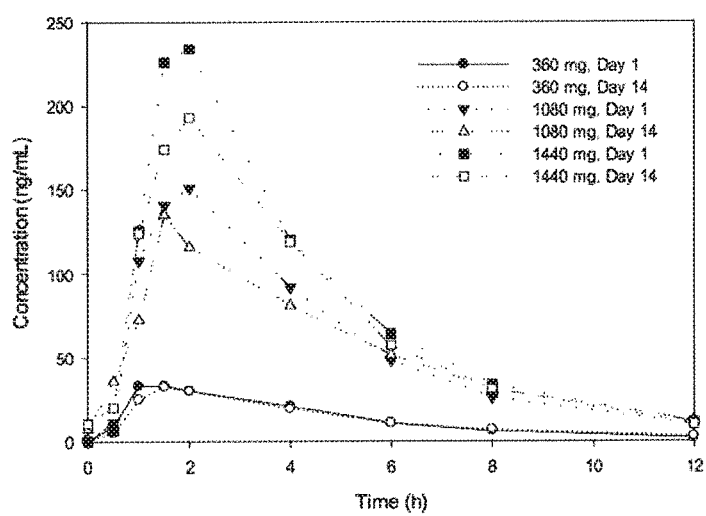
Figure 2. Mean (n = 12 or 13) plasma concentrations of 7-chlorokynurenic acid on Days 1 and 14 after oral administration of once-daily doses of AV-101.

DOSAGE FORMS AND THERAPEUTIC USES OF L-4-CHLOROKYNURENINE

CROSS-REFERENCE TO RELATED APPLICATIONS

This application claims priority to U.S. provisional patent application Ser. No. 61/849,191, filed Jan. 22, 2013 and titled "DOSAGE FORMS AND THERAPEUTIC USES OF L-4-CHLOROKYNURENINE," the content of which is hereby incorporated by reference in its entirety.

STATEMENT REGARDING FEDERALLY SPONSORED RESEARCH

The data presented in this application was supported at least in part by Grant Number 2R44DA018515-02 from the U.S. National Institutes of Health. The government has certain rights in the invention.

FIELD OF THE INVENTION

The present invention relates to compositions of L-4-chlorokynurenine (L-4-Cl-KYN) in unit dose form and to the use of these compositions for the treatment of neurological conditions.

BACKGROUND OF THE INVENTION

Glutamic acid is a major excitatory neurotransmitter in the mammalian central nervous system, and it is involved in the regulation of several different pathways. Associations have been reported between excessive endogenous glutamic acid and various neurological disorders, both acute and chronic, such as cerebral ischemia, epilepsy, amyotrophic lateral sclerosis, Huntington's disease, Parkinson's disease and Alzheimer's disease.

Overactive glutamatergic transmission via N-methyl-D-aspartate (NMDA) receptors (NMDA-R) is known to play a key role in several neurologic conditions, such as neuropathic pain for example. However, direct acting NMDA-R antagonists produce a number of side effects, such as psychosis, which have limited their therapeutic utility. Antagonism of NMDA-Rs can also be achieved through blockade of a modulatory site on the NMDA-R, known as the glycine B (GlyB) coagonist site. (Reference 8, and citations for this reference and the others cited in this manner are presented below). When compared with classic NMDA-R antagonists, GlyB antagonists have a much better safety profile and do not cause the adverse side effects that are associated with "classic" NMDA-R antagonists. (References 1, 6 and 10).

GlyB antagonists also have been shown to reduce hyperalgesia and allodynia in ex vivo and animal neuropathic pain models, and have fewer side effects than classic NMDA-R antagonists, making them a safer alternative as potential analgesics. See, for example, Reference 2.

One of the most potent and specific GlyB antagonists currently known is 7-chlorokynurenic acid (7-Cl-KYNA), which is a synthetic, chlorinated analogue of an endogenous neuromodulator, kynurenic acid. 7-chlorokynurenic acid has been shown to prevent excitotoxic and ischemic neuronal damage but like most GlyB antagonists does not cross the blood-brain barrier. Thus, its clinical use is limited. (References 4 and 9).

In contrast, L-4-chlorokynurenine, a prodrug of 7-chlorokynurenic acid, readily gains access to the central nervous system (CNS) after administration. (References 3, 5, 11 and 12). L-4-chlorokynurenine is efficiently converted to 7-chlorokynurenic acid within activated astrocytes, (Reference 5) and brain levels of 7-chlorokynurenic acid are increased at sites of neuronal injury or excitotoxic insult as a result of astrocyte activation. (Reference 5)

In preclinical studies, L-4-chlorokynurenine has shown anti-seizure activity in rats. (Reference 11). The compound also was found to increase the firing rate and burst firing activity of dopaminergic neurons in the brains of rats. (Reference 7).

Methods for the synthesis of a class of 4,6-disubstituted kynurenines derivatives, including L-4-chlorokynurenine, and their use as antagonists to the NMDA receptor were described in U.S. Pat. No. 5,547,991 to Palfreyman et al. (1996). Pharmaceutical compositions containing these compounds, and their therapeutic use also were described.

SUMMARY OF THE INVENTION

The invention and various embodiments are set out in the claims that form part of this patent application.

Without limiting the foregoing, in a preferred aspect, the invention relates to pharmaceutical compositions that per unit dose consist essentially of L-4-chlorokynurenine in an amount of about 360, 1,080 or 1,440 mg, together with pharmaceutically acceptable ingredients such as carriers and excipients. Another aspect of the invention involves the administration of therapeutically effective amounts of these compounds to treat conditions, disorders and diseases caused by neurological dysfunction.

Another aspect of the invention relates to dosing protocols for the inventive compositions, such as the administration of a daily dose of from 1 to about 14 or from 1 to about 30 days, more preferably from about 7 to about 24 days, and most preferably from about 12 to about 16 days.

Another preferred aspect of the invention relates to compositions and methods for the treatment of depression and for the treatment of various types of pain, including hyperalgesia, by administering a therapeutically effective amount of L-4-chlorokynurenine.

In another aspect, the invention relates to pharmaceutical compositions and associated therapeutic methods of administering L-4-chlorokynurenine in an amount that produces plasma levels of 7-chlorokynurenic acid as described in this application. A preferred aspect of the invention relates to the administration of L-4-chlorokynurenine at a dose sufficient to produce plasma levels of 7-chlorokynurenic acid are in the range of about 15 ng/mL to 550 ng/mL.

Another aspect of the invention relates to combination pharmaceutical product and associated methods that comprise formulations including L-DOPA and the pharmaceutical composition of L-4-chlorokynurenine described in this application, and to their co-administration, either simultaneously or sequentially at dosages described in the application in order to reduce L-DOPA associated dyskinesias.

All references cited herein, including patent applications and publications, are incorporated by reference in their entirety.

BRIEF DESCRIPTION OF THE DRAWINGS

The following figures, which are described below and which are incorporated in and constitute a part of the specification, illustrate exemplary embodiments according to the disclosure and are not to be considered limiting of the scope of the invention, for the invention may admit to other equally effective embodiments. The figures are not neces- FIG. 1 represents the mean (n=12 or 13) plasma concentrations of L-4-chlorokynurenine on days 1 and 14 after oral administration of once-daily doses of L-4-chlorokynurenine.

FIG. 2 represents the mean (n=12 or 13) plasma concentrations of 7-chlorokynurenic acid on days 1 and 14 after oral administration of once-daily doses of L-4-chlorokynurenine.

DETAILED DESCRIPTION OF THE INVENTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed below are merely representative and do not limit the scope of the invention.

In work supported by a grant from the National Institutes of Health, it was shown that L-4-chlorokynurenine (also known as VistaGen AV-101) had potent antihyperalgesic actions in three animal models of peripheral tissue inflammation and nerve injury with no evidence of side effects. Overall, in animal models, L-4-chlorokynurenine was well tolerated, and produced no safety or toxicity at doses that produce antihyperalgesic effects in animal models.

The present invention is based on the inventors' clinical findings that certain doses of L-4-chlorokynurenine are in fact safe and tolerable in humans without substantial side effects or any significant adverse effects. Moreover, it was surprisingly found that at such dosages, subjects reported relief from neuropathic pain, specifically, hyperalgesia pain. The compound is an antihyperalgesic. It was also surprisingly found that a substantial number of subjects in the clinical study reported positive feelings of "well-being" from the administration of L-4-chlorokynurenine, an indicator of anti-depressive activity, whereas this was not reported by the placebo controls.

The present invention relates to compositions and therapeutic methods to treat various types of neurological disorders, neuropathies (both central and peripheral) and dysfunction such as those caused by: (a) injury and drug toxicities such as result from chemotherapy and anti-viral drugs; (b) diseases and neurodegenerative disorders such as diabetes, cancer, viral infection, Multiple Sclerosis, spondylitis, polyneuritis, surgery, amputation, epilepsy, convulsions, Parkinson's disease, Huntington's disease, and Alzheimer's disease and those diseases and conditions involving overactive glutamatergic transmission via N-methyl-D-aspartate receptors; and (c) imbalances in neurotransmitters, receptors and signaling pathways associated with depression and other psychiatric disorders. The treatment of pain is expressly contemplated, including but not limited to neurogenic pain, spontaneous pain, allodynia hyperalgesia pain, mechanical hyperalgesia pain and heat hyperalgesia pain. Moreover, the treatment of depression is also explicitly contemplated as an aspect of the present invention.

Definitions

"Consisting essentially of" a specified amount of a pharmaceutically active agent means that there is no additional amount of that agent. The presence of other ingredients, for example, excipients and/or lubricants, and the like, or different pharmaceutically active ingredients in combination is not precluded. For example, the combination of L-DOPA with 4-cholorkynurenine is expressly contemplated, as are other compositions and methods for their administration that include 4-chlorokynurenine plus another active ingredient that are given either simultaneously or sequentially but in a time frame in which they have substantially the same therapeutic effect as if they had been administered in a single combination pharmaceutical product.

"Pharmaceutical unit dose," "unit dose" or "unit dose form" means a single dose of L-4-chlorokynurenine, which is capable of being administered to a subject, and which can be readily handled and packaged, remaining as a physically and chemically stable unit dose.

"Therapeutically effective" means that the amount of L-4-chlorokynurenine administered and converted to 7-chlorokinurenic acid acts to down-regulate NMDA-R mediated signal transmission that is sufficient to produce a clinical improvement in neurological function, such as a decrease in neuropathic pain, or an increase in feelings of well-being.

"Without significant adverse effect" means that substantially all patients to whom L-4-chlorokynurenine is administered will have no more than a "mild" adverse event as defined by the U.S. Food and Drug Administration (FDA). The FDA defines a "mild adverse event" as an event that is easily tolerated by the subject, causing minimal discomfort and not interfering with everyday activities. In contrast, a "moderate adverse event" is an event that is sufficiently discomforting causing it to interfere with normal everyday activities.

Pharmaceutical Compositions:

L-4-chlorokynurenine has been synthesized by the methods of Palfreyman et al, U.S. Pat. No. 5,547,991. More recent synthesis processes also have been reported in the medical literature, such as Salituro et al. "Enzyme-Activated Antagonists of the Strychnine-Insensitive Glycine/NMDA Receptor, J. Med. Chem. 1994; 37-334, 336. L-4-chlorokynurenine also is available commercially from various sources, including BOC Sciences (Shirley, N.Y., USA) and Advanced Technology & Industrial Co., Ltd. (Hong Kong, China). Cambridge Major Laboratories (Germantown, Wis., USA) manufactured the L-4-chlorokynurenine used in the clinical study discussed in this patent application.

A preferred embodiment of the invention relates to pharmaceutical compositions comprising a unit dose of a therapeutically effective amount of L-4-chlorokynurenine that is formulated for oral administration, together with pharmaceutically acceptable carriers and excipients.

A pharmaceutical composition of the invention may be formulated in any pharmaceutical form that contains L-4-chlorokynurenine according to the invention and that produces a blood plasma level of 7-chlorokynurenic acid as described in this application. It is contemplated that the exact dosages of L-4-chlorokynurenine to be administered within the ranges described for the present invention are to be safe and effective, and that they produce plasma levels of 7-chlorokynurenic acid resulting from the administration of L-4-chlorokynurenine as described in this patent application at FIG. 2 and in other places. Thus, plasma ranges of 7-chlorokynurenic acid from about 15 ng/mL to about 65 ng/m, from about 65 ng/mL to about 300 ng/mL and from about 300 ng/mL to about 550 ng/mL are expressly contemplated. It is also contemplated that the unit dose formulation of the present invention may be administered one or more times per day, in order to extend the time period in which 4-cholokynurenine levels are elevated to a therapeutically effective amount of 7-cholokynurenic acid.

The unit dose pharmaceutical compositions of L-4-chlorokynurenine for oral administration preferably contain about 50 mg to about 1,800 mg, more preferably about 260 mg to about 1,540 mg, more preferably either about 260 mg to about 460 mg, about 310 mg to about 410 mg, about 980 mg to about 1,180 mg, about 1,030 mg to about 1,130 mg, about 1,340 to about 1,540 mg, about 1,390 mg to about 1,490 mg and most preferably about 360, 1,080 or 1,440 mg.

It is contemplated that the dosing regimens for the compositions of the present invention are therapeutically effective. While a daily dosing regimen is contemplated, as described above, this would preferably be from about 5 to about 30 days, including shorter and longer dosing regimes as determined by a patient's physician. In particular, dosing regimes of about 7 to about 24 days, and about 12 to about 16 days are expressly contemplated.

A preferred aspect of the present invention involves the administration of 4-chlorokynurenine in conjunction with L-DOPA to reduce the dyskinesia associated with maintenance doses (typically, determined empirically for each patient by the physician) of L-DOPA; or to reduce the minimum effective dose of L-DOPA, thereby delaying the onset and/or reducing the severity of the dyskinesia. Pharmaceutical compositions according to the present invention may be administered in combination with L-DOPA, concurrently or closely enough in temporal proximity to ameliorate the side effects of L-DOPA administration. Protocols for the administration of L-DOPA are well known as are associated dyskinesias. See, for example, Tambasco, N. et al "Clinical Aspects and Management of Levodopa-Induced Dyskinesia," Parkinson's Disease 2012, Article ID 745947, doi: 10.1155/2012/745947.

The pharmaceutical composition according to the present invention may be, for example, a tablet, capsule, liquid suspension, solid solution, softgel, injectable, topical, or transdermal, or suppository and nasal delivery. Additionally, a pharmaceutical composition of the present invention can also be a modified release form such as, but not limited to, a bi-modal or extended release form.

In general, the pharmaceutical compositions of the invention may be prepared by conventional methods know in the art of pharmaceutical formulations. For example, see Remington's Pharmaceutical Sciences, 18th Ed., (Mack Publishing Company, Easton, Pa., 1990), which is incorporated herein by reference. In a solid dosage form, L-4-chlorokynurenine may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that may be prepared by mixing the crystalline genistein sodium salt dihydrate according to the invention with, for example, suitable non-irritating excipients or carriers such as cocoa butter, polyethylene glycol or a suppository wax, which may be solid at ordinary temperatures but may be liquid at body temperature and, therefore, melt while in a suitable body cavity and release the active component therein.

Clinical Study:

A Phase 1b, single-site, randomized, double-blind, placebo-controlled, study was conducted involving multiple oral doses of AV-101 in healthy male and female subjects. Subjects were randomized into one of three cohorts (360, 1,080, and 1,440 mg) and received a daily oral dose for 14 consecutive days. Each cohort originally included 12 subjects on active drug and 4 subjects on placebo. The safety, pharmacokinetics (PK), tolerability of treatment, and antihyperalgesic effect of AV-101 on capsaicin-induced hyperalgesia were assessed.

The following PK parameters were derived from the plasma concentration versus time profiles to determine the single-dose and multiple-dose PK profile of AV-101 (L-4-chlorokynurenine) and the active metabolite, 7-chlorokynurenic acid: Maximum concentration (Cmax), Terminal elimination half-life (t½), Time to maximum concentration (Tmax), Area under the plasma study drug concentration versus time curve from Time 0 to time of last measurable concentration (AUC0-t) and Area under the plasma study drug concentration versus time curve from Time 0 extrapolated to infinity (AUC0-∞).

Blood was collected in 6-mL lithium heparin Vacutainer tubes. Samples were centrifuged, and the plasma was separated from the cells and frozen within 30 minutes after centrifugation. Centrifuged samples were placed on ice until they were placed in the freezer. Plasma samples were stored frozen at approximately −20° C. until their shipment to a contractor for analysis.

Baseline samples (0 minutes) were collected before the drug was administered on Day 1 and on Day 14. Samples were then collected at 0.5, 1, 1.5, 2, 4, 6, 8, 12, and 24 hours after dosing on Day 1 and Day 14.

A liquid chromatography with tandem mass spectrometry assay was used for the determination of 7-chlorokynurenic acid and L-4-chlorokynurenine in human plasma. The standard curve range was from 2.00 to 1,000 ng/mL for 7-chlorokynurenic acid, with a lower limit of quantification of 2.00 ng/mL. The standard curve range was from 0.05 to 50 µg/mL for L-4-Cl-KYN with a lower limit of quantification of 0.05 µg/mL. Both assays used a plasma sample volume of 50.0 µL.

The PK of AV-101 were fully characterized across the range of doses in the study. Plasma concentration-time profiles obtained for L-4-chlorokynurenine and 7-chlorokynurenic acid after administration of a single and multiple, once daily oral doses of 360, 1,080, or 1,440 mg were consistent with rapid absorption of the oral close and first-order elimination of both analytes, with evidence of multi-compartment kinetics, particularly for the metabolite 7-chlorokynurenic acid. Mean L-4-chlorokynurenine Tmax values increased with increasing dose level, reaching nearly 2 hours for the highest dose group. Mean t½ values were fairly consistent across doses, ranging from 1.64 to 1.82 hours. Mean L-4-chlorokynurenine Cmax and AUC0-∞ values appeared to be approximately dose linear, although not proportional. Mean Cmax values on Day 1 ranged from 27.7 µg/mL after the 360-mg dose to 64.4 µg/mL after the 1,440-mg dose. Mean AUC0-t values on Day 1 ranged from 64 µg·h/ml, after the lowest dose to 196 µg·h/mL after the 1,440-mg dose. Mean Cmax and AUC0-t values the majority of the times were slightly lower on Day 14 than those on Day 1.

In general, as expected for a metabolite, 7-chlorokynurenic acid maximum concentrations occurred at the same time or later than those for L-4-chlorokynurenine, with mean Tmax values ranging from 1.67 to 2.34 hours. This is shown in FIGS. 1 and 2. Mean t½ values, ranging from 2.52 to 3.23 hours, were slightly more variable across doses than those for L-4-chlorokynurenine. Mean t½ values did not appear to be dose related. Mean 7-chlorokynurenic acid Cmax and AUC0-t values also appeared to be approximately dose linear. Mean Cmax values on Day 1 ranged from 42.7 ng/mL after the 360-mg dose to 314 ng/mL after the 1,440-mg dose. Mean AUC0-t values on Day 1 ranged from 156 ng·h/mL after the lowest dose to 985 ng·h/mL after the 1,440-mg dose. Similar to the parent compound, mean Cmax and AUC0-t values for 7-chlorokynurenic acid generally were slightly lower on Day 14 than those on Day 1.

Example 1: Antihyperalgesic Effect of L-4-Chlorokynurenine on Capsaicin-Induced Hyperalgesia On Day 1 and Day 14 of the clinical study, two intradermal injections of 250 µg of capsaicin were injected sequentially into the volar aspect of alternate forearms to produce burning pain, secondary hyperalgesia, and a flare. The capsaicin USP (United States Pharmacopeia) was prepared according to the site's standard procedure and dissolved in 20% cyclodextrin at a concentration of 10 mg/mL.

The first capsaicin injection in one forearm was given 1 hour after oral administration of AV-101 or placebo, and the second capsaicin injection was given in the other forearm 2 hours after the administration of AV-101 or placebo. The neurosensory testing began immediately at each capsaicin injection. The serial pain assessments using a 100-mm visual analog scale (VAS) occurred at preinjection and 0, 5, 10, 15, 30, 45, and 60 minutes after each capsaicin injection. The examiner asked the subject to rate the intensity by using the VAS of the spontaneous pain and elicited pain from the application of a 5.18 von Frey hair, 40° C. probe, and gentle stroking with a 1-inch foam brush. The VAS consisted of a 100-mm line with "no pain" written at the 0-mm end and the "worst imaginable pain" written at the 100-mm end. The distance in millimeters provided the pain measurement.

The borders of the hyperalgesic area to a 5.18 von Frey hair were determined by moving from an area of the skin that did not produce pain tangentially toward the center of the painful area at a progressively closer radius until the subject reported pain or tenderness. At least eight determinations of the hyperalgesic area borders were made using the same assessments and starting at different angles. Additionally, subjects were asked to rate the pain intensity of a 1-minute 45° C. heat stimulus (brief thermal stimulation) applied to the anterior thigh at 4.5 hours (±5 minutes) after study drug administration, then every 30 minutes (±5 minutes) through 6 hours after study drug administration. A radiant temperature probe was applied to fix the skin temperature at 36° C. during the pain assessments. Subjects used the VAS for all pain assessments.

All study assessment time points were anchored to Time 0, the time of study drug administration. For the capsaicin injection at 1 hour after dosing, the assessment interval (i.e., time after dosing of the study drug) was 60 to 120 minutes, during which time assessments occurred at approximately 60, 65, 70, and 75 minutes and then every 15 minutes through the 120-minute time point (i.e., 0, 5, 10, 15, 30, 45, and 60 minutes after capsaicin injection). The second injection of capsaicin was administered approximately 2 hours after dosing of the clinical trial material (CTM), and the assessment interval (i.e., time after dosing of the CTM) was 120 to 180 minutes. The serial pain assessments followed the same schedule, as described after the first capsaicin injection.

The primary efficacy endpoint was the analgesic response to spontaneous pain at each dose level of AV-101 120 to 180 minutes after dosing on Day 14. There was no significant change in the area under the pain time curve (AUPC) for the spontaneous pain assessment between the treatment and the placebo groups. Likewise, there were no significant changes between the treatment and the placebo groups for any of the secondary efficacy endpoints (AUPC for spontaneous pain for the time interval of 120 to 180 minutes after dosing on Day 1; and AUPC for spontaneous pain, elicited pain from the von Frey hair, and elicited pain from the 40° C. probe for the time interval of 60 to 180 minutes after dosing on Days 1 and 14). However, the present inventors found a consistent decrease in the least squares means of the AUPC for allodynia pain, mechanical hyperalgesia pain, and heat hyperalgesia pain between subjects that received 1,080 mg AV-101 (Cohort 2) and subjects that received placebo. These data are shown in Table 1.

TABLE 1

Pain evaluation scores

| | n | MAXPAIN | MP StdDiv |
|---|---|---|---|
| Heat Allogesia | | | |
| placebo | 4 | 84.75 | 5.74 |
| 1080 mg | 13 | 78.85 | 16.22 |
| Mechanical Allogesia | | | |
| placebo | 4 | 79.75 | 7.93 |
| 1080 mg | 13 | 66.23 | 25.60 |
| Allodynia Pain (foam brush) | | | |
| placebo | 4 | 79.50 | 9.68 |
| 1080 mg | 13 | 70.92 | 21.63 |
| Spontaneous Pain | | | |
| placebo | 4 | 77.00 | 10.23 |
| 1080 mg | 13 | 75.08 | 23.33 |

Example 2: Anti-Depressive Activity of L-4-Chlorokynurenine

The present inventors surprisingly also found a mood enhancing or anti-depressive activity of L-4-chlorokynurenine. In the clinical study described in this application, 5 out of 26 subjects (as contrasted with zero subjects in the placebo group) affirmatively reported feelings of well being. This is consistent with reports that the glutamatergic system contributes to the pathophysiology of depression and that stress can induce changes in NMDA receptors. See, for example, Calabrese et al. "Stress-Induced Changes of Hippocampal NMDA Receptors: Modulation by Duloxetine Treatment," PLoS ONE 2012, 7(5): e37916. doi:10.1371/journal.pone.0037916.

In summary, the invention described in this application generally relates to dosage forms of L-4-chlorokynurenine and methods for treating neurological conditions characterized by overactive glutamatergic transmission mediated by N-methyl-D-aspartate receptors, as described above. While certain exemplary embodiments have been described above in detail and shown in the accompanying drawing figures, it is to be understood that such embodiments are merely illustrative of and not restrictive of the broad invention. In particular, it should be recognized that the teachings of the invention apply to a wide variety of diseases. Persons of skill in the art will recognize that various modifications may be made to the illustrated and other embodiments of the invention described above, without departing from its broad inventive scope. Thus, it will be understood that the invention is not limited to the particular embodiments or arrangements disclosed, but is rather intended to cover any changes, adaptations or modifications which are within the scope and spirit of the invention as defined by the appended claims.

REFERENCES

The following journal articles and all other publications, patents and texts mentioned in this application are incorporated by reference in their entireties.
(1) Carter A J. Glycine antagonist: Regulation of the NMDA receptor channel complex by the strychnine-insensitive glycine site. Drugs Future 1992; 17:595-613.
(2) Catarzi et al., Competitive Gly/NMDA receptor antagonists, Curr. Top. Med. Chem. 2006; 6(8):809-21.
(3) Hokari M, Wu H-Q, Schwarez R, Smith Q R. Facilitated brain uptake of 4-chlorokynurenine and conversion to 7-chlorokynurenic acid. Neuroreport 1996; 8(1):15-18.
(4) Kemp J A, Foster A C, Leeson P D, Priestley T, Tridgett R, Iversen L L, et al. 7-Chlorokynurenic acid is a selective antagonist at the glycine modulatory site of the N-methyl-D-aspartate receptor complex. Proc Natl Acads Sci U.S.A. 1988; 85(17):6547-6550.
(5) Lee S-C, Schwarez R. Excitotoxic injury stimulates pro-drug-induced 7-chlorokynurenate formation in the rat striatum in vivo. Neuroscience Lett 2001; 304(3):185-188.
(6) Leeson P D, Iversen L L. The glycine site on the NMDA receptor: Structure-activity relationships and therapeutic potential. J Med Chem 1994; 37(24):4053-4067.
(7) Linderholm, et al., Activation of rat ventral tegmental area dopamine neurons by endogenous kynurenic acid: a pharmacological analysis, Neuropharmacology 2007; 53(8):918-924.
(8) Parsons C G, Danysz W, Quack G, Hartmann S, Lorenz B, Wollenburg C, et al. Novel systemically active antagonists of the glycine site of the N-methyl-D-aspartate receptor: electrophysiological, biochemical and behavioral characterization. J Pharmacol Exp Ther 1997; 283 (3):1264-1275.
(9) Rao T S, Gray N M, Dappen M S, Cler J A, Mick S J, Emmett M R, et al. Indole-2-carboxylates, novel antagonists of the N-methyl-D-aspartate (NMDA)-associated glycine recognition sites: in vivo characterization. Neuropharmacol 1993; 32(2):139-147.
(10) Rundfeldt C, Wlaz P, Loscher W. Anticonvulsant activity of antagonists and partial agonists for the NMDA receptor-associated glycine site in the kindling model of epilepsy. Brain Res 1994; 653(1-2):125-130.
(11) Wu H Q, Lee S C, Scharfman H E, Schwarcz R. L-4-chlorokynurenine attenuates kainate-induced seizures and lesions in the rat. Exp Neurol 2002; 177(1): 222-232.
(12) Wu H-Q, Lee S-C, Schwarcz R. Systemic administration of 4-chlorokynurenine prevents quinolinate neurotoxicity in the rat hippocampus. Eur J Pharm 2000; 390:267-274.

We claim:

1. A method for ameliorating the side effect of dyskinesia induced by the administration of L-DOPA to a subject comprising the administration of a therapeutically effective amount of L-4-chlorokynurenine to the subject.

2. The method of claim 1 wherein the L-4-chlorokynurenine is administered as a pharmaceutical composition that per unit dose consists essentially of L-4-chlorokynurenine in an amount of about 50 to about 1,800 mg and a pharmaceutically acceptable ingredient.

3. The method of claim 2 wherein the L-4-chlorokynurenine is administered as a pharmaceutical composition that per unit dose consists essentially of L-4-chlorokynurenine in an amount of about 360 to about 1,440 mg.

4. The method of claim 3 wherein the pharmaceutical unit dose form is a tablet or a capsule.

5. The method of claim 3 wherein the pharmaceutical composition that per unit dose consists essentially of L-4-chlorokynurenine in an amount of about 360, 1,080 or 1,440 mg.

6. The method of claim 1, wherein the L-4-chlorokynurenine is orally administered.

* * * * *